(12) United States Patent
Koizumi et al.

(10) Patent No.: US 6,875,591 B1
(45) Date of Patent: Apr. 5, 2005

(54) PROCESS FOR PRODUCING GDP-FUCOSE

(75) Inventors: Satoshi Koizumi, Tokyo (JP); Hiroshi Nagano, Yamaguchi (JP); Tetsuo Endo, Tokyo (JP); Kazuhiko Tabata, Yamaguchi (JP); Akio Ozaki, Yamaguchi (JP)

(73) Assignee: Kyowa, Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/631,709

(22) Filed: Aug. 3, 2000

(30) Foreign Application Priority Data

Aug. 10, 1999 (JP) .......................................... 11-225889

(51) Int. Cl.$^7$ .......................... C12P 19/30; C12P 19/32; C12P 19/02
(52) U.S. Cl. ............................. 435/89; 435/92; 435/105
(58) Field of Search ............................. 435/105, 92, 89

(56) References Cited

FOREIGN PATENT DOCUMENTS

| EP | 0 870 841 | | 10/1998 |
|---|---|---|---|
| WO | 99/09180 | * | 2/1999 |
| WO | WO 99/36555 | | 7/1999 |

OTHER PUBLICATIONS

Carbohydrate Research, vol. 242 (1993), pp. 69–76.
Agric. Biol. Chem., vol. 48 (1984), pp. 823–824.
Biochim. Biophys. Act., vol. 117 (1966), pp. 79–87.
FEBS Letters, vol. 412 (1997), pp. 126–130.
Journal of Bacteriology, vol. 179, No. 4 (1997), pp. 1298–1306.
Journal of Bacteriology, vol. 178, No. 16 (1996), pp. 4885–4893.
Journal of Bacteriology, vol. 176, No. 18 (1994), pp. 5847–5851.
Gene, vol. 28 (1984), pp. 337–342.

* cited by examiner

*Primary Examiner*—Sandra E. Saucier
(74) *Attorney, Agent, or Firm*—Fitzpatrick, Cella, Harper & Scinto (57) ABSTRACT

Processes for producing GDP-fucose, comprising allowing GKDM and a culture broth of a microorganism capable of converting GKDM into GDP-fucose to be present in an aqueous medium, forming and accumulating GDP-fucose therein, and recovering the GDP-fucose therefrom; or comprising allowing a GTP precursor, a saccharide, a culture broth of a microorganism capable of forming GTP from a GTP precursor, and a culture broth of a microorganism capable of forming GKDM from a saccharide and GTP to be present in an aqueous medium, forming and accumulating GKDM therein, converting the accumulated GKDM into GDP-fucose using as a culture broth of a microorganism capable of converting GKDM into GDP-fucose to form and accumulate GDP-fucose therein, and recovering the GDP-fucose therefrom; and a process for producing GKDM, comprising allowing a GTP precursor, a saccharide, a culture broth of a microorganism capable of forming GTP from a GTP precursor, and a culture broth of a microorganism capable forming GKDM from a saccharide and GTP to be present in an aqueous medium, forming and accumulating GKDM therein, and recovering the GKDM therefrom.

25 Claims, 3 Drawing Sheets

PROCESS FOR PRODUCING GDP-FUCOSE

BACKGROUND OF THE INVENTION

1. Field of the Invention

The present invention relates to processes for producing guanosine 5'-diphospho-fucose (hereinafter referred to as "GDP-fucose") and guanosine 5'-diphospho-4-keto-6-deoxymannose (hereinafter referred to as "GKDM") GDP-fucose is useful, for example, as a synthetic substrate of complex carbohydrates which are useful, for example, for application to and immunotherapy for the protection against infections by bacteria, viruses and the like and cardiovascular diseases. Also, GKDM is useful as, for example, an intermediate for the production of GDP-fucose.

2. Brief Description of the Background Art

As a process for producing GDP-fucose, a chemical synthesis process (*Carbohyd. Res.*, 242: 69 (1993)) is known; however, it has disadvantages in terms of stereoselectivity and the supply of a substrate. The processes in which enzymes are used (*Agric. Biol. Chem.*, 48: 823 (1984), WO 93/08205, and WO 99/09180) are not suitable for large scale production since they use expensive materials. Also, the enzymes require complex purification steps. A process using the activity of a microorganism has been developed (WO 98/12343) and is a useful process; however, it requires further modification for use as an industrial production process. In addition, it is known that the activity of GDP-mannose 4,6-dehydratase as the starting enzyme in the biosynthesis of GDP-fucose from GDP-mannose is inhibited by the final product, GDP-fucose (*Biochim. Biophys. Acta*, 117: 79 (1966); *FEBS Lett.*, 412: 126 (1997)).

SUMMARY OF THE INVENTION

An object of the present invention is to provide efficient processes for producing GDP-fucose and GKDM.

This object and others are provided by the present invention, which relates to the following (1) to (18).

(1) A process for producing GDP-fucose, comprising:
allowing GKDM and an enzyme source to be present in an aqueous medium, wherein the enzyme source is a culture broth of a microorganism capable of converting GKDM into GDP-fucose or a treated product of the culture broth;
forming and accumulating GDP-fucose in the aqueous medium; and
recovering the GDP-fucose from the aqueous medium.

(2) A process for producing GDP-fucose, comprising:
allowing a guanosine 5'-triphosphate (hereinafter referred to as "GTP") precursor, a saccharide and enzyme sources to be present in an aqueous medium, wherein the enzyme sources are a culture broth of a microorganism capable of forming GTP from a GTP precursor or a treated product of the culture broth, and a culture broth of a microorganism capable of forming GKDM from a saccharide and GTP or a treated product of the culture broth;
forming and accumulating GKDM in the aqueous medium;
converting the accumulated GKDM into GDP-fucose using, as an enzyme source, a culture broth of a microorganism capable of converting GKDM into GDP-fucose or a treated product of the culture broth to form and accumulate GDP-fucose in the aqueous medium; and
recovering the GDP-fucose from the aqueous medium.

(3) A process for producing GKDM, comprising:
allowing a GTP precursor, a saccharide and enzyme sources to be present in an aqueous medium, wherein the enzyme sources are a culture broth of a microorganism capable of forming GTP from a GTP precursor or a treated product of the culture broth, and a culture broth of a microorganism capable forming GKDM from a saccharide and GTP or a treated product of the culture broth,
forming and accumulating GKDM in the aqueous medium; and
recovering the GKDM from the aqueous medium.

(4) The process according to (1), (2) or (3), wherein the treated product of the culture broth is selected from the group consisting of a concentrated product of the culture broth, a dried product of the culture broth, cells obtained by centrifuging the culture broth, a dried product of the cells, a freeze-dried product of the cells, a surfactant-treated product of the cells, an ultrasonic wave-treated product of the cells, a mechanical grinding-treated product of the cells, a solvent-treated product of the cells, an enzyme-treated product of the cells, a protein fraction of the cells, an immobilized product of the cells, and an enzyme preparation obtained by extracting from the cells.

(5) The process according to (2) or (3), wherein the GTP precursor is selected from the group consisting of guanine, xanthine, hypoxanthine, guanosine, xanthosine, inosine, guanosine 5'-monophosphate, xanthosine 5'-monophosphate, and inosine 5'-monophosphate.

(6) The process according to (2) or (3), wherein the saccharide is selected from the group consisting of glucose, fructose, and mannose.

(7) The process according to (2) or (3), wherein the microorganism capable of forming GTP from a GTP precursor is selected from microorganisms belonging to the genus *Corynebacterium*.

(8) The process according to (7), wherein the microorganism is *Corynebacterium ammoniagenes*.

(9) The process according to (2) or (3), wherein the microorganism capable of forming GKDM from a saccharide and GTP is at least one kind of microorganisms.

(10) The process according to (9), wherein the at least one kind of microorganisms is at least one microorganism selected from microorganisms belonging to the genera *Escherichia* and *Corynebacterium*.

(11) The process according to (10), wherein the microorganism belonging to the genus *Escherichia* is *Escherichia coli*.

(12) The process according to (10), wherein the microorganism belonging to the genus *Corynebacterium* is *Corynebacterium ammoniagenes*.

(13) The process according to (2) or (3), wherein the microorganism capable of forming GKDM from a saccharide and GTP is a microorganism having a strong activity of at least one enzyme selected from the group consisting of glucokinase (hereinafter referred to as "glk"), phosphomannomutase (hereinafter referred to as "manB"), mannose 1-phosphate guanylyltransferase (hereinafter referred to as "manC"), phosphoglucomutase (hereinafter referred to as "pgm"), phosphofructokinase (hereinafter referred to as "pfk"), and GDP-mannose 4,6-dehydratase (hereinafter referred to as "gmd").

(14) The process according to (13), wherein the microorganism is at least one microorganism having a recombinant DNA comprising a vector and a DNA fragment containing at least one gene selected from the group consisting of a glk-encoding gene, a manB-encoding gene, a manC-encoding gene, a pgm-encoding gene, a pfk-encoding gene, and a gmd-encoding gene.

(15) The process according to (14), wherein the glk-encoding gene, the manB-encoding gene, the manC-encoding gene, the pgm-encoding gene, the pfk-encoding gene or the gmd-encoding gene is a gene derived from *Escherichia coli*.

(16) The process according to (1) or (2), wherein the microorganism capable of converting GKDM into GDP-fucose is a microorganism having strong GKDM epimerase/reductase (hereinafter referred to as "wcaG") activity.

(17) The process according to (16), wherein the microorganism is a microorganism having a recombinant DNA comprising a vector and a DNA fragment containing a wcaG-encoding gene.

(18) The process according to (17), wherein the wcaG-encoding gene is derived from *Escherichia coli*.

DETAILED DESCRIPTION OF THE INVENTION

This application is based on Japanese application No. Hei 11-225889 filed on Aug. 10, 1999, the entire contents of which is incorporated hereinto by reference.

In order to achieve the above and other objects, the present inventors have conducted intensive studies, and found that the inhibition of GDP-mannose 4,6-dehydratase activity by GDP-fucose can unexpectedly be avoided, and therefore GDP-fucose can be formed efficiently, by forming and accumulating GKDM, (a precursor of GDP-fucose), and then converting the thus accumulated GKDM into GDP-fucose.

The process is preferably conducted in the culture broth of a microorganism capable of forming GTP from a GTP precursor or a treated product of the culture broth. Any microorganism can be used so long as it is a microorganism having such an ability. Appropriate GTP precursors are well-known, and include those described later. Examples of such microorganisms include those belonging to the genus *Escherichia* and the genus *Corynebacterium*.

Examples of the microorganisms belonging to the genus *Escherichia* include *Escherichia coli* and the like. Examples of the microorganisms belonging to the genus *Corynebacterium* include *Corynebacterium ammoniagenes* and the like. Specific examples include *Corynebacterium ammoniagenes* ATCC 21170 and the like.

Also, the process is preferably conducted in the culture broth of a microorganism capable of forming GKDM from a saccharide and GTP or a treated product of the culture broth. Appropriate saccharides are also well-known, and include those described later. Examples of such microorganisms include those having a strong activity of at least one enzyme selected from the group consisting of glk, manB, manC, pgm, pfk and gmd. The above microorganisms having a strong enzyme activity mean microorganisms having an activity of at least one enzyme selected from the group consisting of, for example, glk, manB, manC, pgm, pfk and gmd which has been improved from the activity of a parent strain. The parent strain means a microorganism used as the origin in the construction of a variant, a cell fusion strain, a transductant or a recombinant strain. The microorganisms having an activity of at least one enzyme selected from the above enzymes which has been improved from the activity of the parent strain may be any of a variant, a cell fusion strain, a transductant and a recombinant strain.

Examples thereof include microorganisms belonging to the genus *Escherichia* and the genus *Corynebacterium*. Preferred examples include *Escherichia coli* and *Corynebacterium ammoniagenes*.

Additionally, a transformant in which an activity of at least one enzyme selected from glk, manB, manC, pgm, pfk and gmd is improved by recombinant DNA techniques can also be used. Examples thereof include *Escherichia coli* NM522 having a recombinant DNA (pNK11) containing a glk gene derived from *Escherichia coli* (*J. Bacterial.*, 179: 1298 (1997)), *Escherichia coli* NM522 having a recombinant DNA (pNK11) containing a manB gene derived from *Escherichia coli* (*J. Bacteriol.*, 178: 4885 (1996)), *Escherichia coli* NM522 having a recombinant DNA (pNK11) containing a manC gene derived from *Escherichia coli* (*J. Bacteriol.*, 178: 4885 (1996)), *Escherichia coli* NM522 having a recombinant DNA (pNT55) containing a pgm gene derived from *Escherichia coli* (*J. Bacteriol.*, 176: 1298 (1994)) (WO 98/12343), *Escherichia coli* NM522 having a recombinant DNA (pNT55) containing a pfkB gene derived from *Escherichia coli* (*Gene*, 28: 337 (1984)) (WO 98/12343), *Escherichia coli* NM522 having a recombinant DNA (pGE19) containing a gmd gene derived from *Escherichia coli* (*J. Bacteriol.*, 178: 4885 (1996)), and the like.

When a microorganism is capable of forming GTP from a GTP precursor and is also capable of forming GKDM from a saccharide and GTP simultaneously, GKDM can then be formed by the microorganism from a GTP precursor and a saccharide. Also, in the case of a microorganism which has only a part of the activities necessary for forming GKDM from a saccharide and GTP in one strain, GKDM can be formed by appropriately combining at least two microorganisms.

Any microorganism can be used as the microorganism capable of converting GKDM into GDP-fucose used in the present invention, so long as it has such a converting activity. For example, a microorganism having a strong wcaG activity can be used.

Specifically, a microorganism belonging to the genus *Escherichia* or the genus *Corynebacterium*, such as *Escherichia coli*, *Corynebacterium ammoniagenes*, or the like, can be exemplified.

Furthermore, a transformant in which activities of GKDM epimerase/reductase are improved by recombinant DNA techniques can also be used. Examples thereof include *Escherichia coli* NM522 having a recombinant DNA (pGE8) containing an *Escherichia coli* wcaG gene (*J. Bacteriol.*, 178: 4885 (1996)).

In the above production of GDP-fucose and GKDM using recombinant DNA techniques, various processes related to genetic recombination, such as isolation and purification of a plasmid DNA from a microorganism, digestion of the plasmid DNA with restriction enzymes, isolation and purification of the digested DNA fragment, enzymatic ligation of the DNA fragments, transformation using a recombinant DNA, and the like, can be carried out in accordance with known processes (e.g., *Molecular Cloning, A Laboratory Manual, Second Edition*, Cold Spring Harbor Laboratory Press (1989) (hereinafter referred to as "*Molecular Cloning, Second Edition*") and *Current Protocols in Molecular Biology*, John Wiley & Sons (1987–1997) (hereinafter referred to as "*Current Protocols in Molecular Biology*")).

Also, a polymerase chain reaction (hereinafter referred to as "PCR") can be carried out in accordance with a known process (*PCR Protocols*, Academic Press (1990)).

A gene related to the formation of GDP-fucose or GKDM can be expressed in a host by making a DNA fragment containing the gene into a DNA fragment having an appropriate length containing the gene with restriction enzymes or by the PCR, inserting the resulting fragment into the downstream of the promoter of an appropriate expression vector, and then introducing the DNA-inserted expression vector into a host cell suitable for the expression vector.

Any of bacteria, yeast and the like can be used as the host cell, so long as it can express the gene of interest.

Examples of the expression vector include those capable of replicating autonomously in the above-described host cell or capable of being integrated into chromosome, and containing a promoter at the position where the gene of interest can be transcribed.

When a prokaryote, such as a bacterium or the like, is used as the host cell, it is preferred that the gene expression vector can replicate autonomously in the prokaryote and is a recombinant DNA which is constructed from a promoter, a ribosome binding sequence, a DNA of interest and a transcription termination sequence. It may contain a gene which controls the promoter.

Examples of the expression vector include pKK223-3 and pGEX-2T (both manufactured by Amersham Pharmacia Biotech Co.), pSE280 (manufactured by Invitrogen Co.), pGEMEX-1 (manufactured by Promega Co.), pQE-30 (manufactured by Quiagen Co.), pET-3 (manufactured by Novagen Co.), pKYP10 (Japanese Published Unexamined Patent Application No. 110600/83), pKYP200 (*Agric. Biol. Chem.*, 48: 669 (1984)), pLSA1 (*Agric. Biol. Chem.*, 53: 277 (1989)), pGEL1 (*Proc. Natl. Acad. Sci., USA*, 82: 4306 (1995)), pBluescript II SK+ (manufactured by Stratagene Co.), pBluescript II SK– (manufactured by Stratagene Co.), pTrS30 (prepared from *Escherichia coli* JM109/pTrS30 (FERM BP-5407)), pTrS32 (prepared from *Escherichia coli* JM109/pTrS32 (FERM BP-5408)), pUC19 (*Gene*, 33: 103 (1985)), pSTV28 (manufactured by Takara Shuzo Co., Ltd.), pUC118 (manufactured by Takara Shuzo Co., Ltd.), pPAC31 (WO 98/12343), and the like.

Any promoter can be used, so long as it can function in host cells, such as *Escherichia coli* and the like. Examples thereof include promoters derived from a bacterium or phage, such as trp promoter (Ptrp), lac promoter (Plac) $P_L$ promoter ($P_L$), $P_R$ promoter, $P_{SE}$ promoter, and the like, SPO1 promoter, SPO2 promoter, penP promoter, and the like. Further examples include artificially designed and modified promoters, such as a promoter prepared by connecting two Ptrp's in series, tac promoter, lac T7 promoter, and let I promoter.

It is preferred to use a plasmid in which the space between the Shine-Dalgarno sequence which is a ribosome binding sequence and the initiation codon is controlled at an appropriate distance (e.g., 6 to 18 bases).

In the recombinant DNA of the present invention, the transcription termination sequence is not always necessary for the expression of the DNA of interest; however, it is preferred to arrange the transcription termination sequence just below the structural gene.

Examples of the prokaryote include microorganisms belonging to the genus *Escherichia, Serratia, Bacillus, Brevibacterium, Corynebacterium, Microbacterium, Pseudomonas*, and the like. Specific examples include *Escherichia coli* XL1-Blue, *Escherichia coli* XL2-Blue, *Escherichia coli* DH1, *Escherichia coli* MC1000, *Escherichia coli* W1485, *Escherichia coli* NM522, *Escherichia coli* JM109, *Escherichia coli* HB101, *Escherichia coli* No. 49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium immariophilum* ATCC 14068, *Brevibacterium saccharolyticum* ATCC 14066, *Corynebacterium ammoniagenes, Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, *Pseudomonas* sp. D-0110, and the like.

As the process for introducing a recombinant DNA, any process can be used, so long as it is a process for introducing the DNA into the host cell, such as a process using a calcium ion (*Proc. Natl. Acad. Sci., USA*, 69: 2110 (1972)), a protoplast process (Japanese Published Unexamined Patent Application No. 248394/88), an electroporation process (*Nucleic Acids Research*, 16: 6127 (1988)), and the like.

When a yeast strain is used as the host cell, examples of used expression vector include YEp13 (ATCC 37115), YEp24 (ATCC 37051), YEp50 (ATCC 37419), pHS19, pHS15, and the like.

Any promoter can be used, so long as it can function in the yeast strain. Examples thereof include PH05 promoter, PGK promoter, GAP promoter, ADH promoter, gal 1 promoter, gal 10 promoter, heat shock polypeptide promoter, MFα1 promoter, CUP 1 promoter, and the like.

Examples of the host cell include yeast strains belonging to the genus *Saccharomyces, Schizosaccharomyces, Kluyveromyces, Trichosporon, Schwanniomyces, Pichia, Candida*, and the like. Specific examples include *Saccharomyces cerevisiae, Schizosaccharomyces pombe, Kluyveromyces lactis, Trichosporon pullulans, Schwanniomyces alluvius, Pichia pastoris, Candida utilis*, and the like.

As the process for introducing the recombinant DNA, any process can be used, so long as it is a process for introducing the DNA into yeast. Examples thereof include an electroporation process (*Methods in Enzymol.*, 194: 182 (1990)), a spheroplast process (*Proc. Natl. Acad. Sci. USA*, 81: 4889 (1984)), a lithium acetate process (*J. Bacteriol.*, 153: 163 (1983)), and the like.

Culturing of the transformant of the present invention in a medium can be carried out in accordance with a process generally used for culturing a host.

As the medium for culturing the transformant obtained using a prokaryote, such as *Escherichia coli* or the like, or a eucaryote, such as yeast or the like, as the host, any one of natural media and synthetic media can be used, so long as it contains a carbon source, a nitrogen source, inorganic salts and the like which can be assimilated by the organism and can perform culturing of the transformant efficiently.

Any material which can be assimilated by the organism can be used as the carbon source. Examples thereof include carbohydrates (e.g., glucose, fructose, sucrose, molasses containing them, starch, starch hydrolysate, etc.), organic acids (e.g., acetic acid, propionic acid, etc.), alcohols (e.g., ethanol, propanol, etc.), and the like.

Examples of the nitrogen source include ammonia, ammonia salts of inorganic or organic acids (e.g., ammonium chloride, ammonium sulfate, ammonium acetate, ammonium phosphate, etc.), other nitrogen-containing compounds, peptone, meat extract, yeast extract, corn steep liquor, casein hydrolysate, soybean meal, soybean meal hydrolysate, various fermented cells and digests thereof, and the like.

Examples of inorganic materials used in the medium include potassium dihydrogen phosphate, dipotassium hydrogen phosphate, magnesium phosphate, magnesium sulfate, sodium chloride, ferrous sulfate, manganese sulfate, copper sulfate and calcium carbonate.

The culturing is carried out generally under aerobic conditions, such as shaking culture, submerged aeration agitation culture, and the like. The culturing temperature is preferably from 15 to 40° C., and the culturing time is generally from 5 hours to 7 days. During the culturing, the medium pH is controlled at from 3.0 to 9.0. The pH is adjusted by an inorganic or organic acid, an alkali solution, urea, calcium carbonate, ammonia, or the like.

In addition, antibiotics, such as ampicillin and chloramphenicol, and the like, may be optionally added to the medium during culturing.

When a microorganism transformed with an expression vector in which an inducible promoter is used as the promoter is cultured, an inducer may be optionally added to the medium. For example, when a microorganism transformed with an expression vector using lac promoter is cultured, isopropyl-β-D-thiogalactopyranoside may be added to the medium; and when a microorganism transformed with an expression vector using trp promoter is cultured, indole acrylate may be added.

When at least two microorganisms are used in the process of the present invention, such microorganisms may be separately cultured to use the respective culture broths, or they may be simultaneously inoculated into a single culture vessel to carry out mixture culturing and then the resulting culture broth is used. Alternatively, during or after completion of the culturing of any one of the microorganisms, the remaining microorganism is inoculated and cultured and the resulting culture broth is used.

A microbial culture broth obtained by the culturing or a treated product of the culture broth after its various treatment can be used as an enzyme source in the process of the present invention in an aqueous medium.

Examples of the treated product of the culture broth include a concentrated product of the culture broth, a dried product of the culture broth, cells obtained by centrifuging the culture broth, a dried product of the cells, a freeze-dried product of the cells, a surfactant-treated product of the cells, an ultrasonic wave-treated product of the cells, a mechanical grinding-treated product of the cells, a solvent-treated product of the cells, an enzyme-treated product of the cells, a protein fraction of the cells, an immobilized product of the cells, an enzyme preparation obtained by extracting from the cells, and the like.

The microorganism in the process of the present invention is used at an amount of from 1 to 500 g/l, preferably from 5 to 300 g/l, as wet cells. Also, when the formation reaction is carried out simultaneously using at least two microorganisms, the amount of the total wet cells of the microorganisms in an aqueous medium is from 2 to 500 g/l, preferably from 10 to 400 g/l.

Examples of the GTP precursor used in the process of the present invention include guanine, xanthine, hypoxanthine, guanosine, xanthosine, inosine, guanosine 5'-monophosphate, xanthosine 5'-monophosphate, inosine 5'-monophosphate, and the like. The precursor which can be used include a purified compound, a salt of the precursor, and a culture broth containing the precursor produced by fermentation of a microorganism or the precursor partially purified from the culture broth, so long as the contaminants do not inhibit the reaction. The GTP precursor is used at a concentration of from 0.1 mM to 1.0 M, preferably from 0.01 to 0.5 M.

Examples of the saccharide used in the process of the present invention include glucose, fructose, mannose, derivatives thereof, and the like. The saccharide may be used as a purified product or a material containing the same, so long as the contaminants do not inhibit the reaction. The saccharide may be added in a lump at the time of starting of the reaction, or dividually or continuously during the reaction. The saccharide used at a concentration of from 0.1 mM to 2.0 M.

In the process of the present invention, an energy donor, a coenzyme, a phosphate ion, a magnesium ion, a chelating agent (e.g., phytic acid, etc.), a surfactant and an organic solvent may be optionally added.

Any compound can be used as the energy donor, so long as it promotes the formation. Examples thereof include carbohydrates (e.g., glucose, fructose, sucrose, lactose, maltose, mannitol, sorbitol, etc.), organic acids (e.g., pyruvic acid, lactic acid, acetic acid, etc.), amino acids (e.g., glycine, alanine, aspartic acid, glutamic acid, etc.), molasses, starch hydrolysate, and the like. The energy donor is used at a concentration of from 1.0 mM to 2.0 M.

Examples of the phosphate ion include orthophosphoric acid, pyrophosphoric acid, tripolyphosphoric acid, polyphosphoric acid, metaphosphoric acid, inorganic phosphates (e.g., potassium dihydrogenphosphate, dipotassium hydrogenphosphate, sodium dihydrogenphosphate, disodium hydrogenphosphate, etc.), and the like. The phosphate ion is used at a concentration of from 1.0 mM to 1.0 M.

Examples of the magnesium ion include inorganic magnesium salts (e.g., magnesium sulfate, magnesium nitrate, magnesium chloride, etc.), organic magnesium salts (e.g., magnesium citrate, etc.), and the lie. The magnesium ion is generally used at a concentration of from 1 to 100 mM.

Any surfactant can be used, so long as it can promote the formation. Examples thereof include nonionic surfactants (for example, polyoxyethylene octadecylamine (e.g., Nymeen S-215, manufactured by NOF CORPORATION), etc), cationic surfactants (for example, cetyltrimethylammonium bromide, alkyldimethyl benzylammonium chloride (e.g., Cation F2-40E, manufactured by NOF CORPORATION), etc.), anionic surfactants (for example, lauroyl sarcosinate, etc.), tertiary amines (for example, alkyldimethylamine (e.g., Tertiary Amine FB, manufactured by NOF Corporation), etc.), and the like, which may be used alone or as a mixture of at least two thereof. The surfactant is generally used at a concentration of from 0.1 to 50 g/l.

Examples of the organic solvent include xylene, toluene, aliphatic alcohol, acetone, ethyl acetate, and the like. The organic solvent is generally used at a concentration of from 0.1 to 50 ml/l.

Examples of the aqueous medium used in the process of the present invention include water, buffers (e.g., buffers of phosphate, carbonate, acetate, borate, citrate, Tris, etc.), alcohols (e.g., methanol, ethanol, etc.), esters (e.g., ethyl acetate, etc.), ketones (e.g., acetone, etc.), amides (e.g., acetamide, etc.), and the like. Alternatively, a culture medium of a microorganism may be used as the aqueous medium.

The process of the present invention is carried out in the aqueous medium for 1 to 96 hours at pH 5 to 10, preferably pH 6 to 8 and at a temperature of 20 to 50° C.

The GDP-fucose and GKDM formed in the aqueous medium can be determined using HPLC or the like in accordance with the process described in WO 98/12343.

The GDP-fucose and GKDM formed in the aqueous medium can be recovered in accordance with a usual process using activated carbon or an ion exchange resin (*Carbohyd. Res.*, 242: 69 (1993)).

Preferred embodiments of the present invention are shown in the following Examples. However, the present invention is not limited thereto.

EXAMPLE 1

Construction of a Strain Expressing glk, manB, manC, pgm and pfkB

A DNA primer having the nucleotide sequence of SEQ ID NO:1 and a DNA primer having the nucleotide sequence of SEQ ID NO:2 were synthesized using a 8905 type DNA synthesizer manufactured by Perceptive Biosystems Co.

Using these synthetic DNA primers, PCR was carried out using a glk gene-containing plasmid pNT46 (WO 98/12343) DNA as a template. The PCR was carried out using 40 μl of a reaction solution containing 1 ng of pNT46 DNA, 0.5 μM of each primer, 2.5 units of Pfu DNA polymerase (manufactured by Stratagene Co.), 4 μl of ×10 buffer for Pfu DNA polymerase (manufactured by Stratagene Co.) and 200 μM of each deoxyNTP, by repeating a cycle of 94° C. for 1 minute, 42° C. for 2 minutes and 72° C. for 3 minutes 30 times.

A 1/10 volume of the reaction solution was subjected to agarose gel electrophoresis to confirm amplification of the fragment of interest and then the remaining reaction solution was mixed with the same volume of TE (10 mM Tris-HCl (pH 8.0) and 1 mM EDTA)-saturated phenol/chloroform (1 vol/1 vol).

After centrifugation of the mixture, the thus obtained upper layer was mixed with two volumes of cold ethanol, and the mixture was allowed to stand at −80° C. for 30 minutes. The resulting solution was centrifuged to obtain a precipitate of DNA.

The precipitate of DNA was dissolved in 20 μl of TE. Using 5 μl of the resulting solution, the DNA was digested with restriction enzymes BGlII and SalI, the resulting DNA fragments were separated by agarose gel electrophoresis, and then a fragment of 1.3 kb was recovered using Gene Clean II Kit.

A manB and manC expression plasmid pNK7 (WO 98/12343) (0.2 μg) was digested with restriction enzymes BamHI and SalI, the DNA fragments were separated by agarose gel electrophoresis, and then a fragment of 8.2 kb was recovered in the same manner.

Using a ligation kit, the fragments of 1.3 kb and 8.2 kb were subjected to a ligation reaction at 16° C. for 16 hours. Using the ligation reaction solution, *Escherichia coli* NM522 was transformed in accordance with the known process described above, and the resulting transformants were spread on an LB agar medium containing 50 μg/ml ampicillin, followed by culturing overnight at 30° C.

Figure 1:
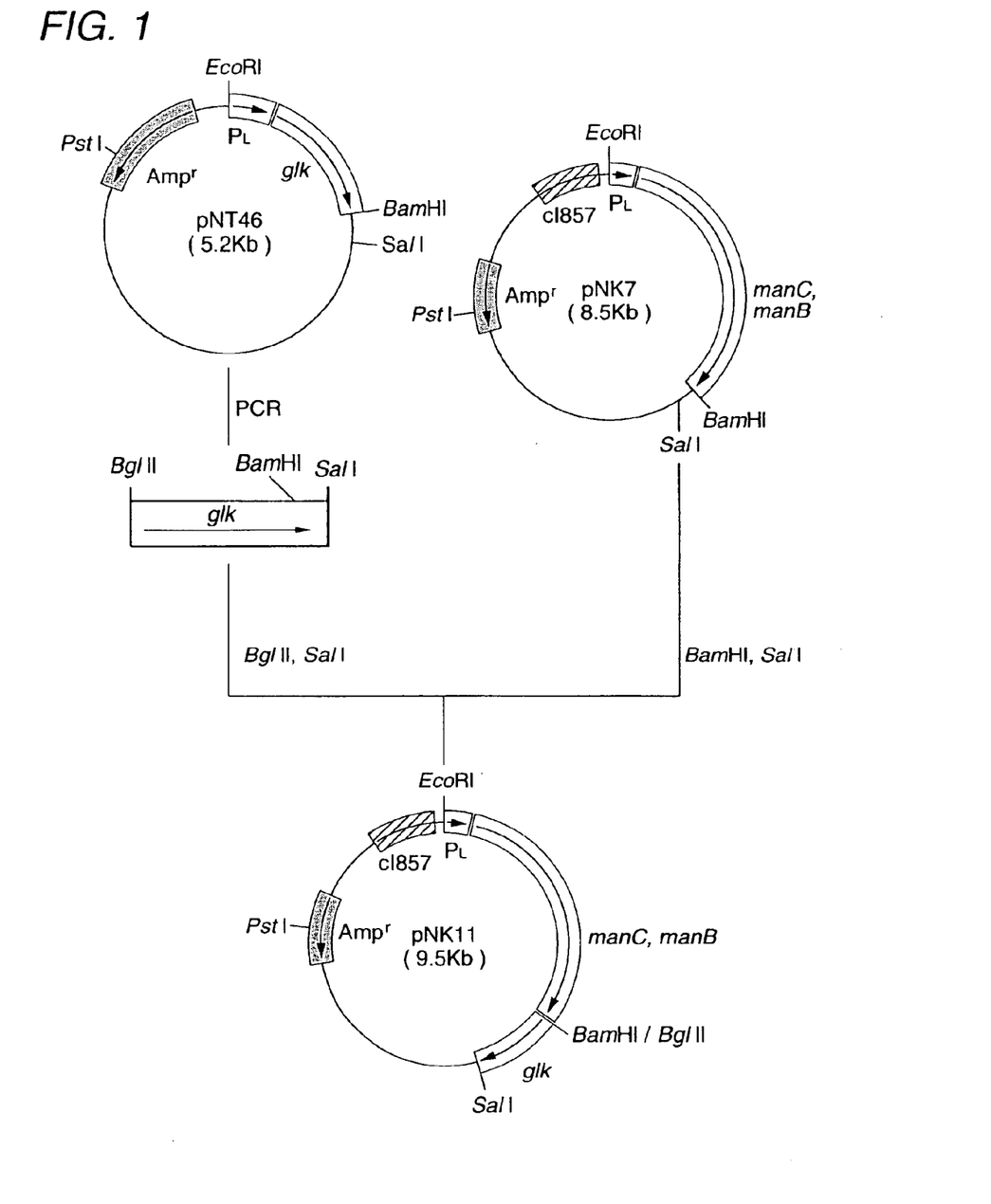
FIG. 1 shows construction steps of a plasmid pNK11 capable of expressing glk, manB and manC.

Plasmids were extracted from the thus grown transformant colonies in accordance with the known process described above to obtain a plasmid pNK11 capable of expressing glk, manB and manC. The structure of this plasmid was confirmed by restriction enzyme digestion (FIG. 1). In FIG. 1, symbols "Amp$^r$" and "cI857" represent an ampicillin-resistant gene and cI857 repressor, respectively.

Using the thus obtained plasmid pNK11, *Escherichia coli* NM522/pNT55 (WO 98/12343) was transformed in accordance with the known process, and the resulting transformants were spread on an LB agar medium containing 50 μg/ml ampicillin and 10 μg/ml chloramphenicol, followed by culturing overnight at 30° C. By selecting the thus grown transformants, *Escherichia coli* NM522/pNK11/pNT55 as a strain capable of simultaneously expressing glk, manB, manC, pgm and pfkB was obtained.

EXAMPLE 2

Construction of a Strain Expressing *Escherichia coli* gmd

*Escherichia coli* W3110 (ATCC 27325) was cultured by the process described in *Current Protocols in Molecular Biology*, and then chromosomal DNA of the microorganism was isolated and purified.

Using DNAs synthesized by the 8905 type DNA synthesizer manufactured by Perceptive Biosystems Co., having the nucleotide sequences of SEQ ID NOs:3 and 4, respectively, as primers, PCR was carried out in accordance with the process described in Example 1 using 0.1 μg of the chromosomal DNA of *Escherichia coli* W3110 (ATCC 27325) as a template.

A 1/10 volume of the reaction solution was subjected to agarose gel electrophoresis to confirm amplification of the fragment of interest, and then the remaining reaction solution was mixed with the same volume of TE-saturated phenol/chloroform.

After centrifugation of the mixture, the thus obtained upper layer was mixed with two volumes of cold ethanol, and the mixture was allowed to stand at −80° C. for 30 minutes. The resulting solution was centrifuged to obtain a precipitate of DNA.

The precipitate of DNA was dissolved in 20 μl of TE. Using 5 μl of the resulting solution, the DNA was digested with restriction enzymes HindIII and XbaI, the resulting DNA fragments were separated by agarose gel electrophoresis, and then a DNA fragment of 1.1 kb was recovered using Gene Clean II Kit.

Using DNA preparations synthesized by the 8905 type DNA synthesizer manufactured by Perceptive Biosystems Co., having the nucleotide sequences of SEQ ID NOs:5 and 6, respectively, as primers, PCR was carried out in accordance with the process described in Example 1 using the DNA of a trp promoter-containing plasmid pNT54 (WO 98/12343) as a template.

A 1/10 volume of the reaction solution was subjected to agarose gel electrophoresis to confirm amplification of the fragment of interest, and then the remaining reaction solution was mixed with the same volume of TE-saturated phenol/chloroform.

After centrifugation of the mixture, the thus obtained upper layer was mixed with two volumes of cold ethanol, and the mixture was allowed to stand at −80° C. for 30 minutes. The resulting solution was centrifuged to obtain a precipitate of DNA, and the precipitate of DNA was dissolved in 20 μl of TE.

Using 5 μl of the resulting solution, the DNA was digested with restriction enzymes EcoRI and XbaI, the resulting DNA fragments were separated by agarose gel electrophoresis, and then a DNA fragment of 0.4 kb was recovered in the same manner.

After 0.2 μg of pBluescriptII SK+ DNA was digested with restriction enzymes EcoRI and HindIII, the DNA fragments were separated by agarose gel electrophoresis, and then a DNA fragment of 3.0 kb was recovered in the same manner.

Using a ligation kit, the fragments of 1.1 kb, 0.4 kb and 3.0 kb were subjected to a ligation reaction at 16° C. for 16 hours.

Using the ligation reaction solution, the *Escherichia coli* NM522 was transformed in accordance with the known process described above, and the resulting transformants were spread on the LB agar medium containing 50 μg/ml ampicillin, followed by culturing overnight at 30° C.

Figure 2:
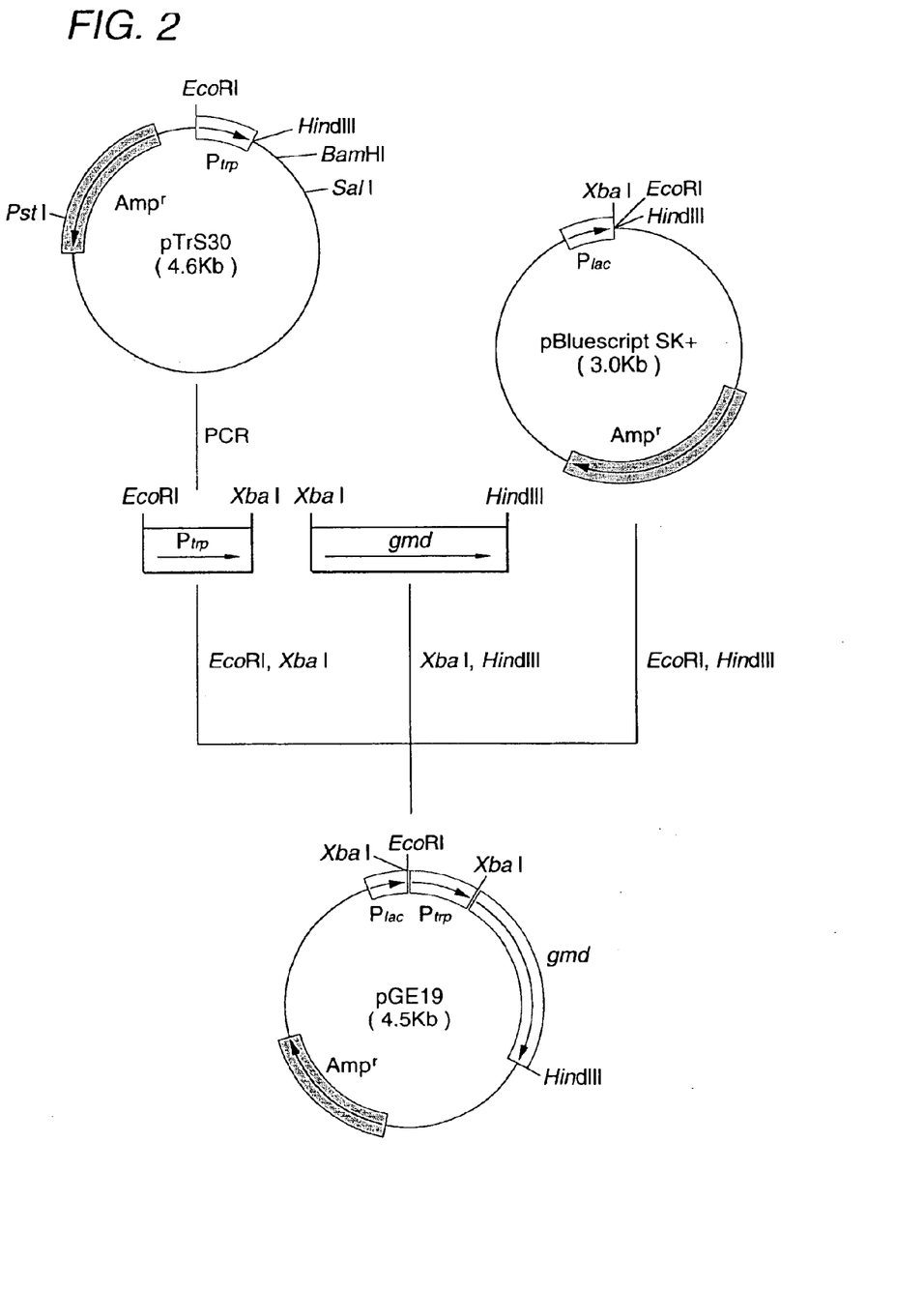
FIG. 2 shows construction steps of a plasmid pGE19 capable of expressing gmd.

Plasmids were extracted from the thus grown transformant colonies in accordance with the known process described above to obtain an expression plasmid pGE19. The structure of this plasmid was confirmed by restriction enzyme digestion (FIG. 2).

EXAMPLE 3

Construction of a Strain Expressing *Escherichia coli* wcaG

Using DNA preparations synthesized by the 8905 type DNA synthesizer manufactured by Perceptive Biosystems Co., having the nucleotide sequences of SEQ ID NOs:7 and 8, respectively, as primers, PCR was carried out in accordance with the process described in Example 1 using the chromosomal DNA of *Escherichia coli* W3110 (ATCC 27325) as a template.

A 1/10 volume of the reaction solution was subjected to agarose gel electrophoresis to confirm amplification of the fragment of interest, and then the remaining reaction solution was mixed with the same volume of TE-saturated phenol/chloroform.

After centrifugation of the mixture, the thus obtained upper layer was mixed with two volumes of cold ethanol, and the mixture was allowed to stand at −80° C. for 30 minutes. The resulting solution was centrifuged to obtain a precipitate of DNA, and the precipitate of DNA was dissolved in 20 μl of TE. Using 5 μl of the resulting solution, the DNA was digested with restriction enzymes ClaI and XhoI, the resulting DNA fragments were separated by agarose gel electrophoresis, and then a DNA fragment of 1.0 kb was recovered using Gene Clean II Kit.

After 0.2 μg of pPAC31 DNA was digested with restriction enzymes ClaI and SalI was digested, the DNA fragments were separated by agarose gel electrophoresis, and then a DNA fragment of 5.2 kb was recovered in the same manner.

Using a ligation kit, the fragments of 1.0 kb and 5.2 kb were subjected to a ligation reaction at 16° C. for 16 hours.

Using the ligation reaction solution, the *Escherichia coli* NM522 was transformed in accordance with the known process described above, and the resulting transformants were spread on the LB agar medium containing 50 μg/ml ampicillin, followed by culturing overnight at 30° C.

Figure 3:
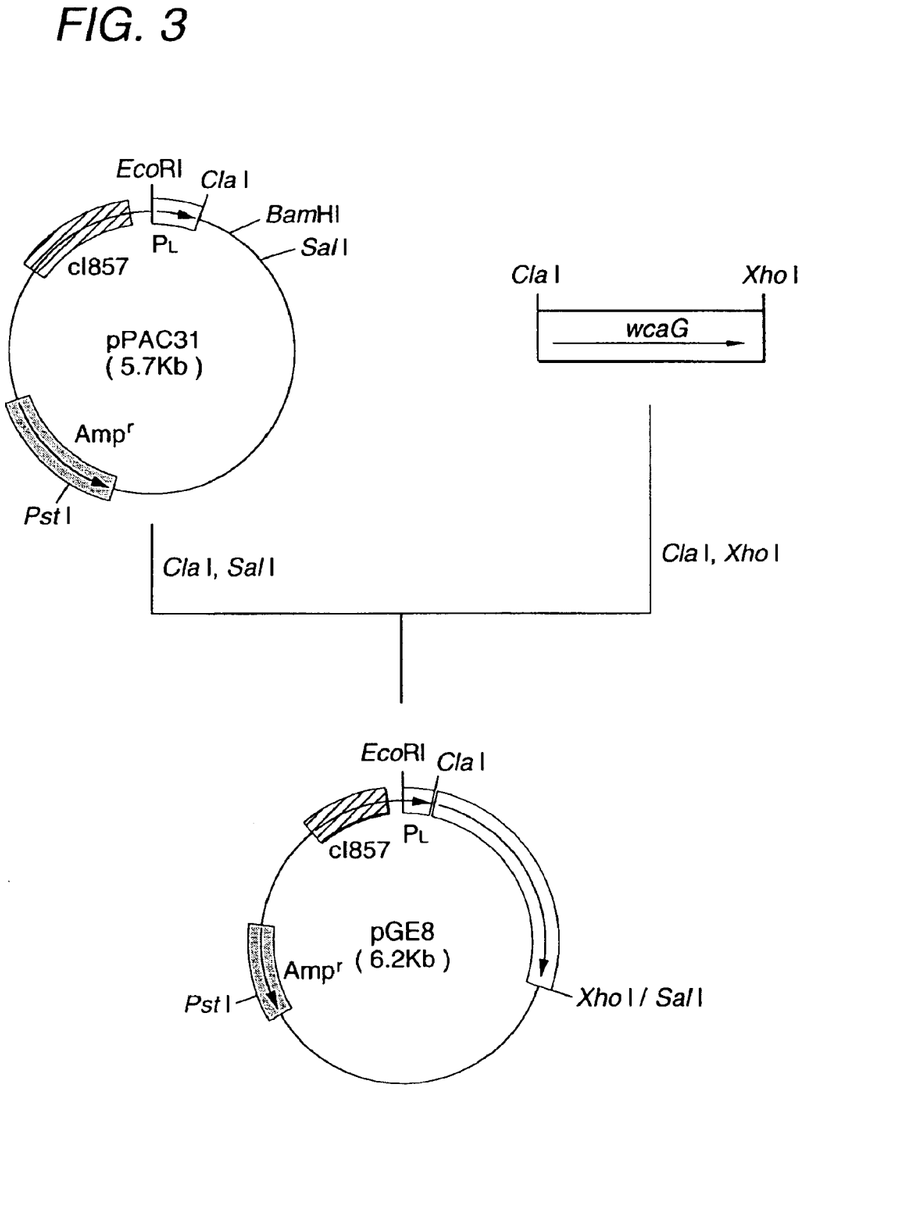
FIG. 3 shows construction steps of a plasmid pGE8 capable of expressing wcaG.

Plasmids were extracted from the thus grown transformant colonies in accordance with the known process described above to obtain an expression plasmid pGE8. The structure of this plasmid was confirmed by restriction enzyme digestion (FIG. 3).

EXAMPLE 4

Production of GKDM

The *Escherichia coli* NM522/pNK11/pNT55 obtained in Example 1 was inoculated into a 1 L baffled conical flask containing 125 ml of LB medium supplemented with 50 μ/ml ampicillin and 10 μg/ml chloramphenicol, followed by culturing at 28° C. and at 220 rpm for 17 hours. The resulting culture broth (125 ml) was inoculated into a 5 L culture vessel containing 2.5 L of a liquid medium (pH not adjusted) composed of 10 g/l glucose, 12 g/l bactotryptone (manufactured by Difco Co.), 24 g/l yeast extract (manufactured by Difco Co.), 2.3 g/l $KH_2PO_4$, 12.5 g/l $K_2HPO_4$ and 50 μg/ml ampicillin, followed by culturing at 30° C. for 4 hours under conditions of 600 rpm and 2.5 L/minute aeration, and further culturing at 40° C. for 3 hours. During the culturing, the medium pH was maintained at 7.0 using 28% aqueous ammonia. Also, glucose was added during the culturing when necessary. The resulting culture broth was centrifuged to obtain wet cells. Since the wet cells can be preserved at −20° C. as occasion demands, it was able to use them by thawing prior to use.

The *Escherichia coli* NM522/pGE19 obtained in Example 2 was inoculated into a 1 L baffled conical flask containing 125 ml of LB medium supplemented with 50 μ/ml ampicillin, followed by culturing at 28° C. and at 220 rpm for 17 hours. The resulting culture broth (125 ml) was inoculated into a 5 L culture vessel containing 2.5 L of a liquid medium (pH not adjusted) composed of 10 g/l glucose, 12 g/l Bactotryptone (manufactured by Difco Co.), 24 g/l yeast extract (manufactured by Difco Co.), 2.3 g/l $KH_2PO_4$, 12.5 g/l $K_2HPO_4$ and 50 μg/ml ampicillin, followed by culturing at 37° C. for 6 hours under conditions of 600 rpm and 2.5 L/minute aeration. During the culturing, the medium pH was maintained at 7.0 using 28% aqueous ammonia. Also, glucose was added during the culturing when necessary. The resulting culture broth was centrifuged to obtain wet cells. Since the wet cells can be preserved at −20° C. as occasion demands, it was able to use them by thawing prior to use.

*Corynebacterium ammoniagenes* ATCC 21170 was inoculated into a 300 ml baffled conical flask containing 25 ml of a liquid medium composed of 50 g/l glucose, 10 g/l polypeptone (manufactured by Nihon Pharmaceutical Co., Ltd.), 10 g/l yeast extract (manufactured by Oriental Yeast Co., Ltd.), 5 g/l urea, 5 g/l $(NH_4)_2SO_4$, 1 g/l $KH_2PO_4$, 3 g/l $K_2HPO_4$, 1 g/l $MgSO_4.7H_2O$, 0.1 g/l $CaCl_2.2H_2O$, 10 mg/l $FeSO_4.7H_2O$, 10 mg/l $ZnSO_4.7H_2O$, 20 mg/l $MnSO_4.4\sim6H_2O$, 20 mg/l L-cysteine, 10 mg/l calcium D-pantothenate, 5 mg/l vitamin $B_1$, 5 mg/l nicotinic acid and 30 μg/l biotin (adjusted to pH 7.2 with 10 N NaOH), followed by culturing at 28° C. and at 220 rpm for 24 hours.

The resulting culture broth (20 ml) was inoculated into a 2 L baffled conical flask containing 250 ml of a liquid medium having the same composition, followed by culturing at 28° C. and at 220 rpm for 24 hours. The thus obtained culture broth was used as a seed culture broth.

The seed culture broth (250 ml) was inoculated into a 5 L culture vessel containing 2.25 L of a liquid medium composed of 150 g/l glucose, 5 g/l meat extract (manufactured by Kyokuto Pharmaceutical Industrial Co., Ltd.), 10 g/l $KH_2PO_4$, 10 g/l $K_2HPO_4$, 10 g/l $MgSO_4.7H_2O$, 0.1 g/l $CaCl_2.2H_2O$, 20 mg/l $FeSO_4.7H_2O$, 10 mg/l $ZnSO_4.7H_2O$, 20 mg/l $MnSO_4.4\sim6H_2O$ (separate sterilization), 15 mg/ml β-alanine (separate sterilization), 20 mg/l L-cysteine, 100 μg/l biotin, 2 g/l urea and 5 mg/l vitamin $B_1$ (separate sterilization) (adjusted to pH 7.2 with 10 N NaOH), followed by culturing at 32° C. for 24 hours under conditions of 600 rpm and 2.5 L/minute aeration. During the culturing, the medium pH was maintained at 6.8 using 28% aqueous ammonia.

The resulting culture broth was centrifuged to obtain wet cells. Since the wet cells can be preserved at −20° C. as occasion demands, it was able to use them by thawing prior to use.

A reaction solution of 25 g/l of the above *Escherichia coli* NM522/pNK11/pNT55 wet cells, 15 g/l of the above

*Escherichia coli* NM522/pGE19 wet cells, 150 g/l of the above *Corynebacterium ammoniagenes* ATCC 21170 wet cells, 60 g/l fructose, 30 g/l mannose, 20 g/l GMP, 25 g/l KH$_2$PO$_4$, 5 g/l MgSO$_4$.7H$_2$O, 5 g/l phytic acid, 4 g/l Nymeen S-215 and 10 ml/l xylene was put into a 200 ml beaker, and the reaction solution was stirred (900 rpm) using a magnetic stirrer to carry out the reaction at 32° C. for 12 hours. During the reaction, the pH of the reaction solution was maintained at 7.2 using 4 N NaOH, and fructose and KH$_2$PO$_4$ were added when necessary.

After completion of the reaction, the reaction product was analyzed by HPLC to confirm that 18.6 g/l (29.4 mM) of GKDM (2Na salt) was formed and accumulated in the reaction solution.

EXAMPLE 5

Production of GDP-fucose

The *Escherichia coli* NM522/pNK11/pNT55 obtained in Example 1 was cultured by the process described in Example 4, followed by centrifuging to obtain wet cells.

The *Escherichia coli* NM522/pGE19 obtained in Example 2 was cultured by the process described in Example 4, followed by centrifuging to obtain wet cells.

The *Escherichia coli* NM522/pGE8 obtained in Example 3 was cultured by a process similar to the *Escherichia coli* NM522/pNK11/pNT55 described in Example 4 except for adding ampicillin only instead of adding ampicillin and chloramphenicol, followed by centrifuging to obtain wet cells.

The *Corynebacterium ammoniagenes* ATCC 21170 was cultured by the process described in Example 4, followed by centrifuging to obtain wet cells.

Since the wet cells can be preserved at −20° C. as occasion demands, it was able to use them by thawing prior to use.

A reaction solution (30 ml) of 25 g/l of the above *Escherichia coli* NM522/pNK11/pNT55 wet cells, 15 g/l of the above *Escherichia coli* NM522/pGE19 wet cells, 150 g/l of the above *Corynebacterium ammoniagenes* ATCC 21170 wet cells, 60 g/l fructose, 30 g/l mannose, 30 g/l GMP, 25 g/l KH$_2$PO$_4$, 5 g/l MgSO$_4$.7H$_2$O, 5 g/l phytic acid, 4 g/l Nymeen S-215 and 10 ml/l xylene was put into a 200 ml beaker, and the reaction solution was stirred (900 rpm) using a magnetic stirrer to carry out the reaction at 32° C. for 12 hours. After 12 hours of the reaction, the *Escherichia coli* NM522/pGE8 wet cells were added to give a concentration of 15 g/l, and the reaction was continued for 10 hours. During the reaction, the pH of the reaction solution was maintained at 7.2 using 4 N NaOH, and fructose and KH$_2$PO$_4$ were added when necessary.

After completion of the reaction, the reaction product was analyzed by HPLC to confirm that 14.0 g/l GDP-fucose was formed and accumulated in the reaction solution.

When the reaction was carried out for 22 hours by adding the *Escherichia coli* NM522/pGE8 (15 g/l) wet cells at the time of starting of the reaction, the amount of the accumulated GDP-fucose (2Na salt) was 3.7 g/l (5.9 mM).

While the invention has been described in detail and with reference to specific embodiments thereof, it will be apparent to one skill in the art that various changes and modifications can be made therein without departing from the spirit and scope thereof.

What is claimed is:

1. A process for producing guanosine 5'-diphosphate-fucose ("GDP-fucose"), comprising:

allowing a guanosine 5'-triphosphate ("GTP") precursor, a saccharide selected from the group consisting of glucose, fructose and mannose, and enzyme sources to be present in an aqueous medium, wherein the enzyme sources are (i) a culture of a microorganism capable of forming GTP from said GTP precursor or a treated product of the culture, and (ii) a culture of a microorganism capable of forming guanosine 5'-diphosphate-4-keto-6-deoxymannose ("GKDM") from said saccharide and GTP or a treated product of the culture;

forming and accumulating GKDM in the aqueous medium; and then adding a culture of a microorganism capable of converting GKDM into GDP-fucose or a treated product of the culture, as an enzyme source, to the aqueous medium to convert the accumulated GKDM into GDP-fucose;

forming and accumulating GDP-fucose in the aqueous medium; and recovering the GDP-fucose from the aqueous medium, wherein the treated products of the culture are treated products independently selected from the group consisting of a concentrated product of the culture, a dried product of the culture, cells obtained by centrifuging the culture, a dried product of the cells, a freeze-dried product of the cells, a surfactant-treated product of the cells, a solvent-treated product of the cells, an enzyme-treated product of the cells and an immobilized product of the cells.

2. The process according to claim 1, wherein the GTP precursor is selected from the group consisting of guanine, xanthine, hypoxanthine, guanosine, xanthosine, inosine, guanosine 5'-monophosphate, xanthosine 5'-monophosphate, and inosine 5'-monophosphate.

3. The process according to claim 1, wherein the microorganism capable of forming GTP from a GTP precursor belongs to the genus *Corynebacterium*.

4. The process according to claim 3, wherein the microorganism is *Corynebacterium ammoniagenes*.

5. The process according to claim 1, wherein the microorganism capable of forming GKDM from a saccharide selected from the group consisting of glucose, fructose and mannose, and GTP is one or more strains of microorganisms.

6. The process according to claim 5, wherein the one or more strains of microorganisms are selected from the genera *Escherichia* and *Corynebacterium*.

7. The process according to claim 6, wherein the microorganism belonging to the genus *Escherichia* is *Escherichia coli*.

8. The process according to claim 6, wherein the microorganism belonging to the genus *Corynebacterium* is *Corynebacterium ammoniagenes*.

9. The process according to claim 1, wherein the microorganism capable of forming GKDM from a saccharide selected from the group consisting of glucose, fructose and mannose, and GTP has a strong activity of at least one enzyme selected from the group consisting of glucokinase ("glk"), phosphomannomutase ("manB"), mannose 1-phosphate guanylyltransferase ("manC"), phosphoglucomutase ("pgm"), phosphofructokinase ("pfk"), and GDP-mannose 4,6-dehydratase ("gmd").

10. The process according to claim 9, wherein the microorganism is at least one microorganism having a recombinant DNA comprising a vector and a DNA fragment containing at least one gene selected from the group consisting of a glk-encoding gene, a manB-encoding gene, a manC-encoding gene, a pgm-encoding gene, a pfk-encoding gene, and a gmd-encoding gene.

11. The process according to claim 10, wherein at least one of the glk-encoding gene, the manB-encoding gene, the manC-encoding gene, the pgm-encoding gene, the pfk-encoding gene or the gmd-encoding gene is derived from *Escherichia coli*.

12. The process according to claim 1, wherein the microorganism capable of converting GKDM into GDP-fucose has strong GKDM epimerase/reductase ("wcaG") activity.

13. The process according to claim 12, wherein the microorganism has a recombinant DNA comprising a vector and a DNA fragment containing a wcaG-encoding gene.

14. The process according to claim 13, wherein the wcaG-encoding gene is derived from *Escherichia coli*.

15. A process for producing guanosine 5'-diphospho-fucose ("GDP-fucose"), comprising:

allowing a guanosine 5'-triphosphate ("GTP"), a saccharide selected from the group consisting of glucose, fructose and mannose, and an enzyme source to be present in an aqueous medium, wherein the enzyme source is a culture of a microorganism capable of forming guanosine 5'-diphosphate-4-keto-6-deoxymannose ("GKDM") from said saccharide and GTP or a treated product of the culture;

forming and accumulating GKDM in the aqueous medium; and then adding a culture of a microorganism capable of converting GKDM into GDP-fucose or a treated product of the culture, as an enzyme source, to the aqueous medium to convert the accumulated GKDM into GDP-fucose;

forming and accumulating GDP-fucose in the aqueous medium; and recovering the GDP-fucose from the aqueous medium, wherein the treated products of the culture are treated products independently selected from the group consisting of a concentrated product of the culture, a dried product of the culture, cells obtained by centrifuging the culture, a dried product of the cells, a freeze-dried product of the cells, a surfactant-treated product of the cells, a solvent-treated product of the cells, an enzyme-treated product of the cells and an immobilized product of the cells.

16. The process according to claim 15, wherein the microorganism capable of forming GKDM from a saccharide selected from the group consisting of glucose, fructose and mannose, and GTP is at least one kind of microorganisms.

17. The process according to claim 16, wherein the at least one kind of microorganisms is at least one microorganism selected from microorganisms belonging to the genera *Escherichia* and *Corynebacterium*.

18. The process according to claim 17, wherein the microorganism belonging to the genus *Escherichia* is *Escherichia coli*.

19. The process according to claim 17, wherein the microorganism belonging to the genus *Corynebacterium* is *Corynebacterium ammoniagenes*.

20. The process according to claim 15, wherein the microorganism capable of forming GKDM from a saccharide selected from the group consisting of glucose, fructose and mannose, and GTP is a microorganism having a strong activity of at least one enzyme selected from the group consisting of glucokinase ("glk"), phosphomannomutase ("manB"), mannose 1-phosphate guanylyltransferase ("manC"), phosphoglucomutase ("pgm"), phosphofructokinase ("pfk") and GDP-mannose 4,6-dehydratase ("gmd").

21. The process according to claim 20, wherein the microorganism is at least one microorganism having a recombinant DNA comprising a vector and a DNA fragment containing at least one gene selected from the group consisting of glk-encoding gene, a manB-encoding gene, a manC-encoding gene, a pgm-encoding gene, a pfk-encoding gene, and a gmd-encoding gene.

22. The process according to claim 21, wherein at least one of the glk-enciding gene, the manB-encoding gene, the manC-encoding gene, the pgm-encoding gene, the pfk-encoding gene or the gmd-encoding gene is derived from *Escherichia coli*.

23. The process according to claim 15, wherein the microorganism capable of converting GKDM into GDP-fucose has strong GKDM epimerase/reductase ("wcaG") activity.

24. The process according to claim 23, wherein the microorganism has a recombinant DNA comprising a vector and a DNA fragment containing a wcaG-encoding gene.

25. The process according to claim 24, wherein the wcaG-encoding gene is derived from *Escherichia coli*.

* * * * *

UNITED STATES PATENT AND TRADEMARK OFFICE
CERTIFICATE OF CORRECTION

PATENT NO.   : 6,875,591 B1
DATED        : April 5, 2005
INVENTOR(S)  : Satoshi Koizumi et al.

It is certified that error appears in the above-identified patent and that said Letters Patent is hereby corrected as shown below:

Column 1,
Line 9, ""GKDM")" should read -- "GKDM"). --.

Column 12,
Line 52, "$_{10}$ g/1 K$_2$HPO$_4$," should read -- 10 g/1 K$_2$HPO$_4$, --.

Column 14,
Line 32, "skill" should read -- skilled --.

Column 19,
Line 13, "glk-enciding" should read -- glk-encoding --.

Signed and Sealed this

Twenty-third Day of August, 2005

JON W. DUDAS
*Director of the United States Patent and Trademark Office*

SEQUENCE LISTING

```
<160> NUMBER OF SEQ ID NOS:  8

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
ccgcaagatc tcgtaaaaag ggtatcgata agc                               33

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gagctgactg ggttgaaggc                                              20

<210> SEQ ID NO 3
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 3
gaatctagaa tgtcaaaagt cgctctc                                            27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ctcaagctta tgactccagc gcgat                                              25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
caagaattct catgtttgac agct                                               24

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
cattctagac ctccttaatt cgcgaaaatg gatcgatacc ctttttac                     48

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
gtcatcgata tgagtaaaca acgagtt                                            27

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ataaactcga gagagacaag cggag                                              25
```